(12) United States Patent
Vitullo et al.

(10) Patent No.: US 8,177,753 B2
(45) Date of Patent: May 15, 2012

(54) CATHETER INSERTION ASSEMBLY

(75) Inventors: Jeffrey M. Vitullo, Pottstown, PA (US);
Newswanger K. Raymond, Terre Hill, PA (US); Eric Lopez, New Tripoli, PA (US)

(73) Assignee: Arrow International, Inc., Reading, PA (US)

( * ) Notice: Subject to any disclaimer, the term of this patent is extended or adjusted under 35 U.S.C. 154(b) by 1294 days.

(21) Appl. No.: 11/756,748

(22) Filed: Jun. 1, 2007

(65) Prior Publication Data

US 2008/0300576 A1    Dec. 4, 2008

(51) Int. Cl.
*A61M 5/178*    (2006.01)
*A61M 25/16*    (2006.01)

(52) U.S. Cl. ......... 604/164.07; 604/164.11; 604/167.03; 604/533

(58) Field of Classification Search ............. 604/164.01, 604/164.04, 164.06, 164.07, 164.09, 164.1, 604/164.11, 164.13, 533, 167.03, 247
See application file for complete search history.

(56) References Cited

U.S. PATENT DOCUMENTS

| | | | |
|---|---|---|---|
| 4,214,593 A | 7/1980 | Imbruce et al. | |
| 4,405,314 A | 9/1983 | Cope | |
| 4,682,978 A | 7/1987 | Martin | |
| 4,894,057 A | 1/1990 | Howes | |
| 4,931,039 A | 6/1990 | Coe et al. | |
| 4,976,691 A | 12/1990 | Sahota | |
| 5,256,146 A | 10/1993 | Ensminger et al. | |
| 5,273,527 A | 12/1993 | Schatz et al. | |
| 5,336,184 A | 8/1994 | Teirstein | |
| 5,372,592 A | 12/1994 | Gambale | |
| 5,382,238 A | 1/1995 | Abrahamson et al. | |
| 5,405,341 A | 4/1995 | Martin | |
| 5,484,407 A | 1/1996 | Osypka | |
| 5,571,087 A | 11/1996 | Ressemann et al. | |
| 5,571,094 A | 11/1996 | Sirhan | |
| 5,919,175 A | 7/1999 | Sirhan | |
| 5,957,912 A | 9/1999 | Heitzmann | |
| 5,980,484 A | 11/1999 | Ressemann et al. | |
| 6,059,771 A | 5/2000 | Balbierz et al. | |
| 6,117,117 A | 9/2000 | Mauch | |
| 6,287,291 B1 | 9/2001 | Bigus et al. | |
| 6,500,152 B1 * | 12/2002 | Illi | 604/164.07 |
| 6,592,569 B2 | 7/2003 | Bigus et al. | |
| 6,638,242 B2 | 10/2003 | Wilson et al. | |
| 6,695,832 B2 | 2/2004 | Schon et al. | |
| 6,712,807 B2 | 3/2004 | Stivland et al. | |
| 6,723,084 B1 | 4/2004 | Maginot et al. | |
| 6,730,096 B2 | 5/2004 | Basta | |
| 6,786,891 B2 * | 9/2004 | Hiejima | 604/164.01 |
| 6,916,310 B2 | 7/2005 | Sommerich | |
| 6,926,721 B2 | 8/2005 | Basta | |
| 6,966,886 B2 | 11/2005 | Appling | |

(Continued)

*Primary Examiner* — Kevin C Sirmons
*Assistant Examiner* — William Carpenter
(74) *Attorney, Agent, or Firm* — Baker & Hostetler LLP

(57) ABSTRACT

A catheter insertion assembly for inserting a catheter into a body lumen of a patient is disclosed as well as a method of using the assembly. The assembly comprises a hub, a catheter stiffener and a valve. The valve is disposed in the lumen of the hub and prevents substantially all fluid flow through the lumen in at least one direction below a pressure threshold. The proximal end of the stiffener is attached to the hub and the stiffener extends distally of the distal end of the hub. The stiffener lumen is in fluid communication with the hub lumen. The stiffener occupies a lumen of the catheter and provides additional stiffness to the catheter such that a catheter introducer is not necessary for insertion of the catheter.

16 Claims, 8 Drawing Sheets

U.S. PATENT DOCUMENTS

| | | |
|---|---|---|
| 6,991,625 B1 | 1/2006 | Gately |
| 6,997,899 B2 | 2/2006 | Scopton |
| 7,066,925 B2 | 6/2006 | Gately |
| 2002/0055732 A1 | 5/2002 | Wilson |
| 2004/0082935 A1 | 4/2004 | Lee et al. |
| 2004/0116852 A1 | 6/2004 | Scopton |
| 2005/0038413 A1* | 2/2005 | Sansoucy ..................... 604/537 |
| 2008/0214993 A1* | 9/2008 | Haarala et al. .................. 604/44 |
| 2009/0112167 A1* | 4/2009 | Haarala et al. ........... 604/167.03 |

* cited by examiner

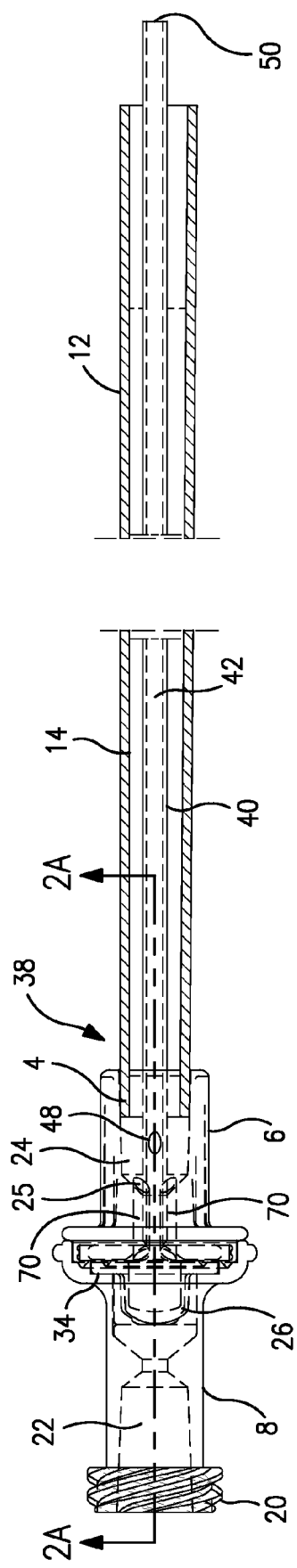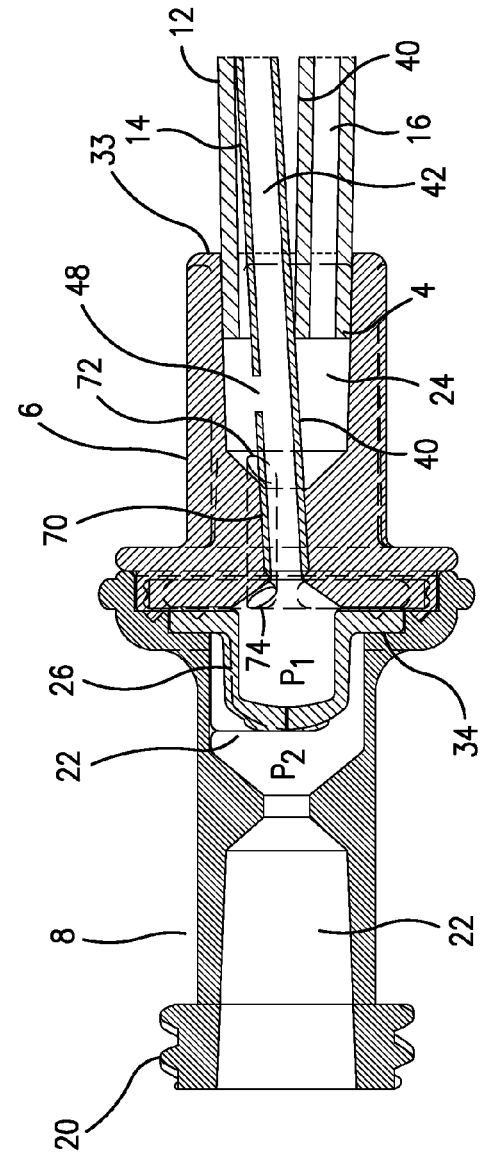
FIG. 2
FIG. 2A

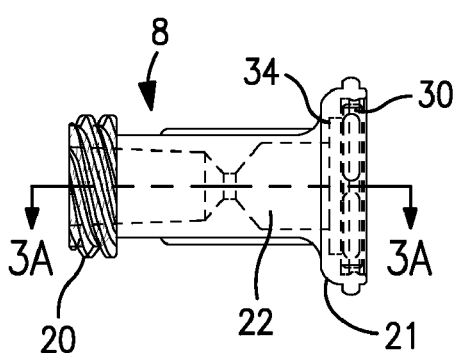
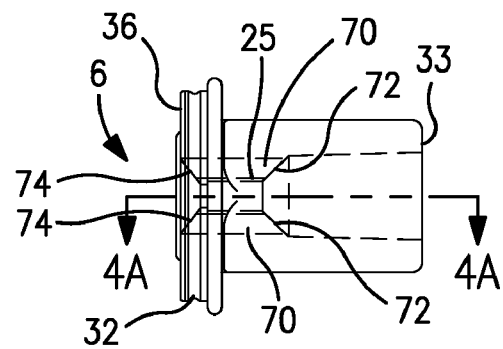
FIG. 3
FIG. 4
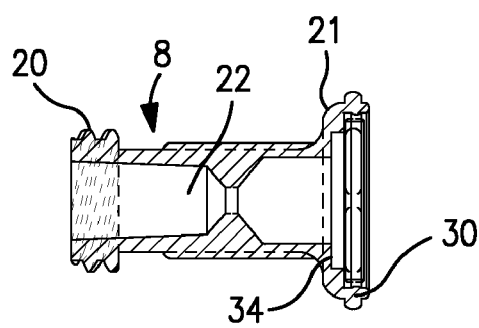
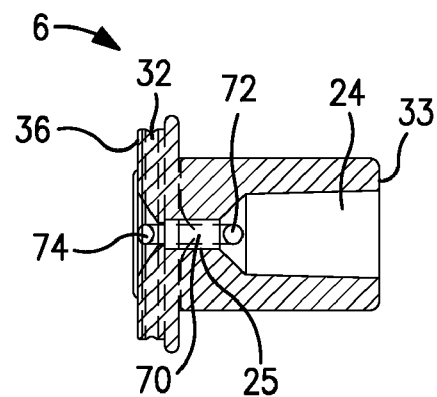
FIG. 3A
FIG. 4A
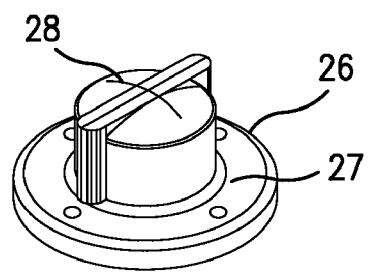
FIG. 5

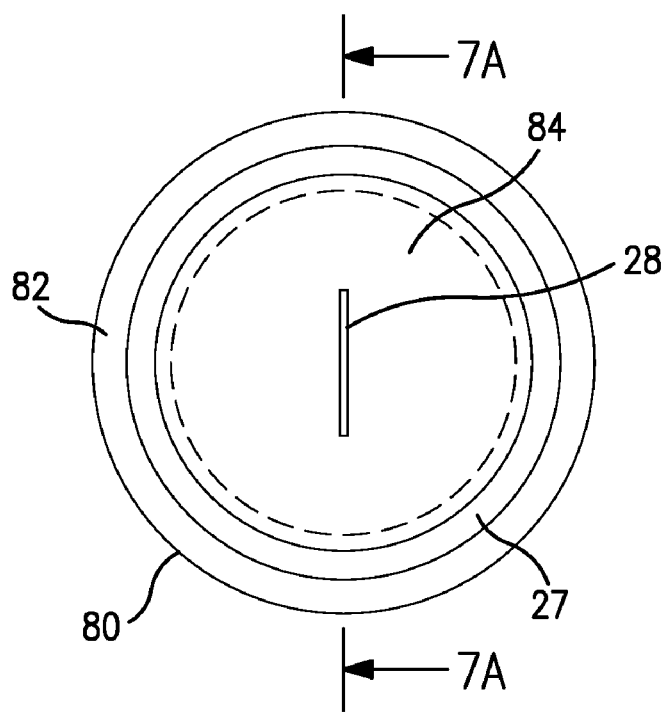 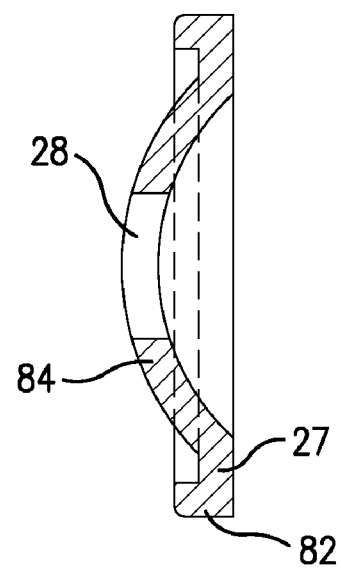
FIG. 7   FIG. 7A

CATHETER INSERTION ASSEMBLY

BACKGROUND OF THE INVENTION

The present invention relates to a catheter insertion assembly for use in placing a catheter into a patient with minimal trauma to the tissues of the patient, particularly at the insertion site, and with a reduced likelihood of air embolism.

Peripherally inserted central venous catheters ("CVCs") have been utilized by clinicians for several decades. Catheter insertion by the Seldinger technique has been used even longer, primarily for the insertion of subclavian and other chest inserted catheters. The Seldinger technique begins with obtaining access to a blood vessel with a needle. The needle is hollow and, after it is determined that the needle has been inserted into the appropriate blood vessel, a wire is passed through the needle bore into the blood vessel. The wire is often referred to as a "guidewire" since its ultimate purpose is to guide a catheter into place. Once it is determined that the distal end of the guidewire is properly placed within the blood vessel, the needle is removed by backing the needle over the guidewire while leaving the guidewire in place. Proper placement of the guidewire may be verified by fluoroscopy or other imaging method.

The guidewire is then used to guide a dilator, if needed, into the blood vessel to widen the opening through the skin and subcutaneous tissue. After use, the dilator is removed while the guidewire is still held in place. Multiple dilators may be used, one after the other, until the opening is large enough to receive a catheter introducer. The catheter introducer is a short hollow tube which is placed in the opening. The introducer is sometimes disposed about the largest dilator and inserted along with the dilator. When the dilator is removed the introducer remains. Alternatively, the catheter introducer is inserted subsequent to the removal of the final dilator. With the introducer in place, the catheter is advanced over the guidewire and through the introducer. When catheter insertion is accomplished, the introducer is pulled out of the incision and split according to the manufacturer's usage directions so that it can be removed from around the catheter. The guidewire is removed either prior to or after the removal of the introducer.

One reason why a catheter introducer is necessary is that most catheters are soft and subject to bending and kinking. Inserting a soft and pliable catheter through the tissue of an insertion site and into the vasculature of a patient, even over a guidewire and after the use of one or more dilators, is difficult. Such an insertion can result in damage to the catheter, to the patient or both.

One of the complications encountered during the insertion of catheters, and particularly insertion of catheters into the patient's thoracic cavity, i.e. adjacent the heart, is the possibility of air embolism. An air embolism is the obstruction of a blood vessel by an air bubble. When inserting a catheter into the vasculature of a patient utilizing the Seldinger technique, a path from the atmosphere to the vasculature is created. While it is usually possible to keep the path sufficiently obstructed, this is not always the case. Whether through necessity or accident, this path is sometimes opened. If, while this path is opened, the patient takes a deep breath, air will be sucked into the central vessels through the open path. This results in an air embolism. Air embolism is potentially a very serious complication and may be fatal.

The likelihood of an air embolism is greatest when a catheter introducer is used. One reason for this is that the diameter of a catheter introducer is usually relatively large, i.e. 12 french or more, in order to fulfill its function of allowing insertion of the catheter. It would defeat the purpose of the catheter introducer to include an obstruction therein; as a clear path from outside of the patient's body to the patient's vasculature needs to be available for the catheter to be inserted. Thus, a need exists for a catheter insertion assembly that reduces insertion trauma and the likelihood or severity of air embolism during catheter insertion into a patient. A need also exists for a catheter insertion assembly that obviates the need for a catheter introducer.

SUMMARY OF THE INVENTION

In one aspect of the present invention, a catheter insertion assembly comprises a hub having a proximal end, a distal end and a lumen extending through the hub between the proximal and distal ends. A valve is disposed in the lumen of the hub and, up to a first pressure threshold, the valve prevents substantially all fluid flow through the hub lumen in at least one direction. The hub also includes a hollow stiffener having a proximal end and a distal end. The stiffener extends distally of the distal end of the hub and is adapted to be placed within a catheter to be inserted into a patient.

In a preferred embodiment, the stiffener further includes a lumen extending from the proximal to the distal end of the stiffener, which stiffener lumen is in fluid communication with a distal portion of the hub lumen.

In another preferred embodiment, the hub lumen is divided into a hub lumen distal portion and a hub lumen proximal portion. One or more irrigation tunnels may be provided for liquid exchange between the distal and proximal lumen portions. The irrigation tunnels may supplement the fluid communication between the stiffener lumen and the distal portion of the hub lumen or may be an alternative thereto.

In use, a catheter is disposed over the stiffener and is connected to the hub of the insertion assembly. The catheter may be a single lumen or a multi-lumen catheter. The catheter, disposed over the stiffener of the insertion assembly, is then inserted over a guidewire and into a patient. The guidewire is received in the lumen of the stiffener.

BRIEF DESCRIPTION OF THE DRAWING

The above and related objects, features and advantages of the present invention will be more fully understood by reference to the following detailed description of the presently preferred, albeit illustrative, embodiments of the present invention when taken in conjunction with the accompanying drawing wherein:

FIG. 2 is a side view of the insertion assembly showing some hidden line detail with the catheter shown in cross-section to better show the stiffener;

FIG. 2A is a cross-sectional detail view of a portion of FIG. 2 taken along cross-sectional line 2A-2A;

FIG. 3 is a side view of a portion of the insertion assembly hub showing some hidden line detail;

FIG. 3A is a cross-sectional detail view of FIG. 3 taken along cross-sectional line 3A-3A;

FIG. 4 is a side view of a portion of the insertion assembly hub showing some hidden line detail;

FIG. 4A is a cross-sectional detail view of FIG. 4 taken along cross-sectional line 4A-4A;

FIG. 5 is a perspective view of one embodiment of the valve of the insertion assembly;

FIG. 7 is a front view of an embodiment of the valve of the insertion assembly;

FIG. 7A is a cross-sectional view of the valve of FIG. 7, taken along cross-sectional line 7A-7A;

DETAILED DESCRIPTION OF THE PREFERRED EMBODIMENTS

Structures and methods for using an insertion assembly to insert a catheter are shown. A broad range of catheter types can be utilized in combination with the structures herein described, such as chronic hemodialysis catheters, central ports, tunneled central catheters, or other catheters normally requiring a catheter introducer.

Figure 1:
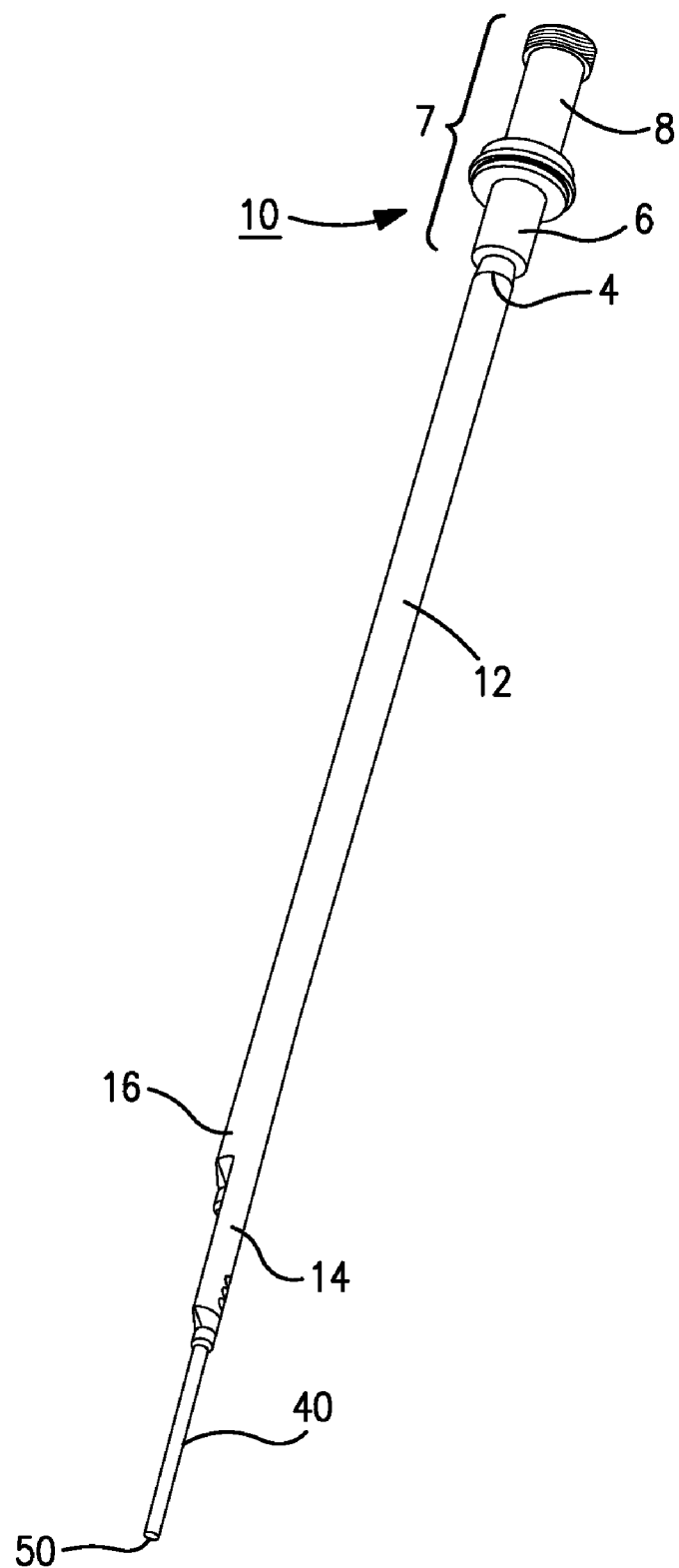
FIG. 1 is a perspective view of the insertion assembly together with a catheter that is to be inserted into a patient.

Referring now to FIG. 1, the insertion assembly 10 is shown together with a catheter 12 which is to be inserted into the patient.

As best seen in FIGS. 1, 2 and 2A, the insertion assembly 10 is made up of a hub 7 which includes stiffener hub portion 6, valve hub portion 8 and valve 26. Any polymer or material with sufficient formability and strength may be used for hub 7, e.g., polycarbonate.

Stiffener 40 extends distally from hub 7, is inserted into catheter 12 and is of such a length as to extend at least the entire length of the catheter 12, and preferably a small distance beyond the distal tip of catheter 12. Stiffener 40 has a stiffness greater than the stiffness of the catheter and therefore stiffens the catheter such that the catheter may be inserted into a patient without buckling, even without using a catheter introducer. This minimizes insertion trauma. A thermoplastic polyurethane resin, e.g. ISOPLAST manufactured by Dow Chemical Company of Midland Mich., is an example of a material of appropriate characteristics to impart the proper stiffness to stiffener 40. For a stiffener made out of thermoplastic polyurethane resin, including a central lumen, and having a diameter of approximately 0.056", a wall thickness of approximately 0.0085" provides satisfactory strength and stiffness characteristics.

Valve 26 is housed within the hub lumen 22, 24. The valve 26 prevents substantially all fluid flow through the hub 7 in at least one direction, e.g. from the atmosphere to inside of the patient, below a first pressure threshold. The catheter 12 is attached to hub 7 such that fluid flow through the lumens of the catheter 12 is controlled by valve 26. As a result, valve 26 prevents substantially all air from entering catheter 12, but can permit fluid flow into the catheter. Thus, the hub 7, stiffener 40 and valve 26 of the insertion assembly 10 cooperate to both minimize insertion trauma and reduce the likelihood of air embolism.

FIGS. 3 and 3A show the structure of the valve hub portion 8 of hub 7. Valve hub portion 8 has a valve hub lumen 22 extending from proximal threaded end 20 to distal connection shoulder 21 near the distal end of the valve hub portion 8. A valve retention collar 34 is located within the connection shoulder 21.

FIGS. 4 and 4A show the structure of the stiffener hub portion 6 of hub 7. Stiffener hub portion 6 has a stiffener hub lumen 24 extending from its proximal end 36 to its distal end 33. The diameter of the inside surface of stiffener hub lumen 24 varies; such that at one point the inside diameter of stiffener hub lumen 24 is of approximately the same diameter as the outside diameter of stiffener 40. In a preferred embodiment of the present invention, stiffener 40 is connected to hub 7 where the inside diameter of stiffener hub lumen 24 is approximately the same as the outside diameter of stiffener 40. This portion of stiffener hub lumen 24 is called the stiffener connection portion 25. Wherever connection between hub 7 and stiffener 40 is made the connection may be, for example, by adhesive, welding, interference fit or press fit.

Stiffener hub portion 6 also has a proximal connection ring 32 adjacent the proximal end 36. If the stiffener hub portion 6 and the valve hub portion 8 are formed separately, then the connection shoulder 21 of valve hub portion 8 engages the connection ring 32 of the stiffener hub portion 6. When this occurs, valve hub portion 8 and stiffener hub portion 6 are connected as a single hub 7 and valve hub lumen 22 is in fluid communication with stiffener hub lumen 24.

FIG. 5 shows valve 26 including an annular shoulder 27 and a valve slit 28 for allowing fluid passage under certain conditions. As best shown in FIGS. 2 and 2A, when valve 26 is installed in hub 7, annular shoulder 27 abuts valve retention collar 34 of valve hub portion 8 and the side of annular shoulder 27 not abutting valve retention collar 34 is abutted by the proximal end 36 of stiffener hub portion 6. Thus, in a preferred embodiment of the present invention, valve 26 is inserted into valve hub portion 8 prior to attachment of stiffener hub portion 6 to valve hub portion 8. Valve retention collar 34 abuts annular shoulder 27 of valve 26, seating valve 26 in valve hub portion 8 and, when stiffener hub portion 6 is attached to valve hub portion 8, valve 26 is trapped in place between valve retention collar 34 and the proximal end 36 of stiffener hub portion 6.

Valve 26 can be made of any pliable material; in a preferred embodiment the valve material is silicone rubber. The function of valve 26 is to prevent unwanted fluid flow through catheter 12 but to allow desirable fluid flow. The term fluid means both liquid and gas. One example of unwanted fluid flow is blood from the patient. However, the primary function of valve 26 is to prevent air from entering the vasculature of the patient from the atmosphere. By preventing substantially all air from flowing from the proximal end of hub 7, which is exposed to the atmosphere during portions of the insertion procedure, to catheter 12, valve 26 prevents air embolism.

While preventing unwanted fluid flow, valve 26 does allow fluid flow under specific, controllable conditions. In a preferred embodiment of the present invention, slit 28 is formed adjacent the center of valve 26. Valve 26 being of a pliable material, e.g. silicone rubber, slit 28 will flex open if a large enough pressure, i.e. a "threshold pressure", is exerted on the slit. The term "cracking pressure" is sometimes used in this context and is synonymous with "threshold pressure" as used herein. Fluid on one side of valve 26 has a first pressure $P_1$, as illustrated in FIG. 2A, and fluid on the other side of valve 26 has a second pressure $P_2$. When the difference between $P_1$ and $P_2$ reaches a specific value, slit 28 flexes open and allows fluid flow from the higher pressure side of the valve to the lesser value pressure side. The specific value of the difference between $P_1$ and $P_2$ is the threshold pressure. Because of the geometry and material characteristics of the valve, there is at least one threshold pressure in each direction and these pressures differ from each other. One purpose of the valve 26 allowing fluid flow is so that all air in the catheter 12 may be displaced prior to insertion. As discussed further below, saline is injected through hub 7 prior to the insertion procedure to remove all air from the assembly 10 and catheter 12. The valve 26, specifically the ability to overcome the seal created by the valve 26, allows this to be accomplished.

Slit 28 in valve 26 also allows passage of a guidewire 60 so that the catheter 12 and stiffener 40 may be moved along the guidewire 60, as will be described below. Threshold pressure will be affected by the presence of guidewire 60, but much of the valve's effectiveness in preventing fluid flow, e.g. air flow into the patient or blood from the patient, should remain in spite of the presence of guidewire 60 extending through slit 28.

Figure 8:
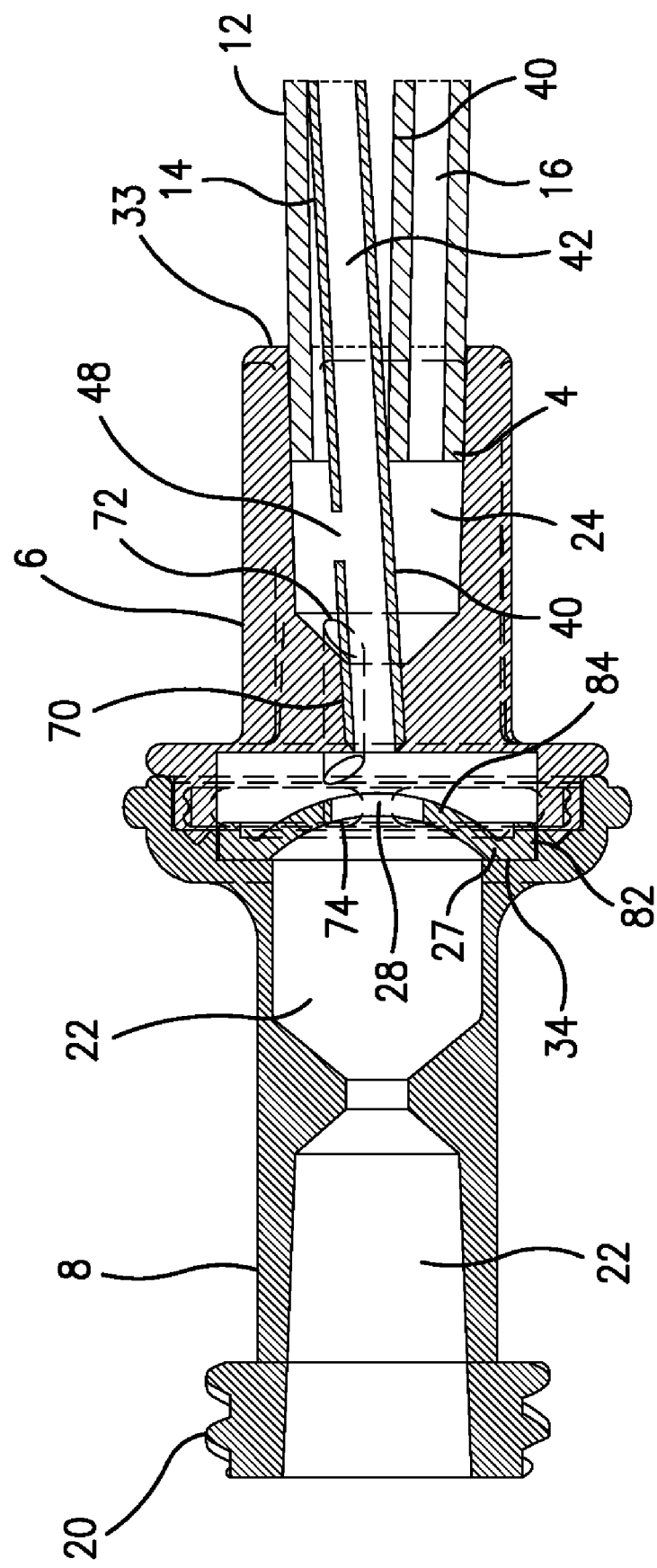
FIG. 8 is a cross-sectional detail view of an alternative embodiment of the insertion assembly utilizing the valve of FIG. 7.

FIGS. 7 and 7A discloses an alternative embodiment of a valve for use in the present invention. Valve 80 shares many of the characteristics of valve 26 including function, material, general placement and interaction with the other structural elements of the present catheter insertion assembly. Valve 80 has a slit 28 in dome portion 84 that has threshold pressures determined by the geometry and material chosen for valve 80 and slit 28. Annular shoulder 27 of valve 80 is provided to interact with portions of hub 7 and be retained in place thereby. Annular ring 82 adds to this retention strength. FIG. 8 shows valve 80 installed in hub 7.

As shown in FIG. 2, stiffener 40 is attached to hub 7 at stiffener connection portion 25 and extends beyond the distal end 33 of hub 7. Stiffener 40 terminates at tip 50 and includes stiffener lumen 42 extending the length of the stiffener 40 from the stiffener proximal end to the tip 50. Stiffener lumen 42 may be used to accommodate a guidewire 60 (such as those used in the Seldinger technique), which guidewire 60 may extend through the entire apparatus shown in FIG. 2, from tip 50 through stiffener lumen 42, valve 26 and hub 7.

As best seen in FIG. 2A, fluid from a fluid supply source (not shown) attached to connection threads 20 passes through valve hub lumen 22 and through valve 26 if valve 26 is opened by a sufficient pressure threshold being overcome. Fluid passing through valve 26 in a distal direction enters stiffener lumen 42. Stiffener 40 may be provided with an irrigation vent 48 adjacent the portion of stiffener 40 attached to stiffener connection portion 25. Irrigation vent 48 allows liquid introduced to the stiffener lumen 42 to exit the stiffener 40 radially very near the connection portion 25.

In an alternative embodiment of the present invention, the stiffener hub portion 6 may be provided with one or more irrigation tunnels 70. The irrigation tunnels 70 connect lumen 22 of valve hub portion 8 to lumen 24 of stiffener hub portion 6 (assuming the threshold pressure of valve 26 is overcome) such that fluid may pass from valve hub lumen 22 to stiffener hub lumen 24 without having to pass through stiffener lumen 42 and stiffener irrigation vent 48.

Irrigation tunnels 70 are shown in FIGS. 2, 2A, 4, 4A and 6. The irrigation tunnels 70 have an axis extending parallel to, though radially offset from, the axis of the stiffener hub lumen 24. Each irrigation tunnel 70 extends from an irrigation tunnel distal hole 72 terminating at stiffener hub lumen 42 to an irrigation tunnel proximal hole 74 terminating at the proximal end 36 of stiffener hub portion 6. The placement of irrigation tunnel proximal holes 74 is such that valve 26 remains effective preventing flow distal of valve slit 28 in appropriate circumstances. Thus, irrigation tunnel 70 provides fluid connection from valve hub lumen 22 to the portion of stiffener hub lumen 24 external to the stiffener 40 that is either alternative or complementary to the fluid connection via stiffener lumen 42 and irrigation vent 48. These fluid connections 48, 70 are used, for example, to displace all air from the insertion assembly 10 and catheter 12 by injecting saline into hub 7 from source connected to connection threads 20.

The catheter to be inserted using insertion assembly 10 may be of essentially any type and have any number of lumens. The catheter 12 shown in FIGS. 1, 2, 2A and 6 is a dual-lumen, step-tip catheter having a longer lumen 14 and a shorter lumen 16. Proximal end 4 of catheter 12 is connected to hub 7. Much of catheter 12 will, eventually, be disposed inside the vasculature of a patient. The proximal end 4 of the catheter 12 will usually remain outside the patient. As discussed further below, the proximal end of catheter 4 can be readily disconnected from hub 7.

After disconnection of proximal end 4 of catheter 12 from hub 7, any of a number of fluid supply and/or removal devices (not shown) can be attached to the proximal end 4 of catheter 12 to allow fluid(s) to be supplied to or removed from the patient. U.S. Pat. No. 6,638,242 discloses a selectively attachable hub that may be attached to proximal end 4 of catheter 12. U.S. Pat. No. 6,638,242 is hereby incorporated by reference in its entirety.

FIG. 2A is a detailed cross-section of FIG. 2 which shows the interconnectivity of the valve hub portion 8, stiffener hub portion 6, stiffener 40 and catheter 12. Stiffener 40 extends through lumen 14 of catheter 12. Stiffener 40 is of a material and/or wall thickness that results in a substantially increased stiffness when disposed in the catheter 12 compared to the stiffness of the catheter 12 alone.

The proximal end 4 of catheter 12 is received in stiffener hub lumen 24 and is connected to hub 7 in any of a number of ways, e.g. adhesive or welding. In a preferred embodiment of the present invention, stiffener hub lumen 24 has a decreasing diameter from its distal end 33 toward stiffener connection portion 25 and is sized for a frictional fit to the proximal end 4 of catheter 12. Proximal end 4 and hub 7 may be disconnected by breaking this connection. Once hub 7 is disconnected from catheter 12, hub 7 as well as stiffener 40 may be discarded.

Irrigation vent 48 in stiffener 40 is, in a preferred embodiment, located between the proximal end 4 of catheter 12 and the stiffener connection portion 25 of stiffener hub lumen 24. Liquid introduced into the stiffener lumen 42 may exit the stiffener 40 radially through irrigation vent 48. Liquid exiting irrigation vent 48 flows into stiffener hub lumen 24, the portion of catheter longer lumen 14 external to the stiffener 40 and catheter shorter lumen 16.

Now that the structures of stiffener apparatus 10 have been described, how the stiffener apparatus 10 is utilized for inserting a catheter 12 may be explained in further detail.

Prior to placement of catheter 12, a liquid source, e.g. a syringe (not shown), may be attached to the connection threads 20 of valve hub portion 8. Liquid introduced into stiffener hub lumen 24 of valve hub portion 8 is given sufficient pressure (via, e.g., the syringe plunger) to pass through valve 26 and enter stiffener lumen 42, which conveys the liquid to the distal tip 50 of catheter 40. Some liquid exits irrigation vent 48 and fills stiffener hub lumen 24 of stiffener hub portion 6 and flows from there into lumen 16 and the portion of lumen 14 external to stiffener 40. Thus, with a single liquid source, every portion of insertion assembly 10 may be filled with liquid.

Using the Seldinger technique or similar methods, a needle (not shown) is passed through the skin 61, subcutaneous tissue 64 and vessel wall 68 of a patient end then used to place guidewire 60. The guidewire 60 is then passed through the needle. The typically j-shaped distal tip 54 of highly flexible guidewire 60 is advanced within the vasculature 66 of the patient to a desired point in the vasculature. This placement is confirmed through a fluoroscope or other imaging technique.

Figure 6:
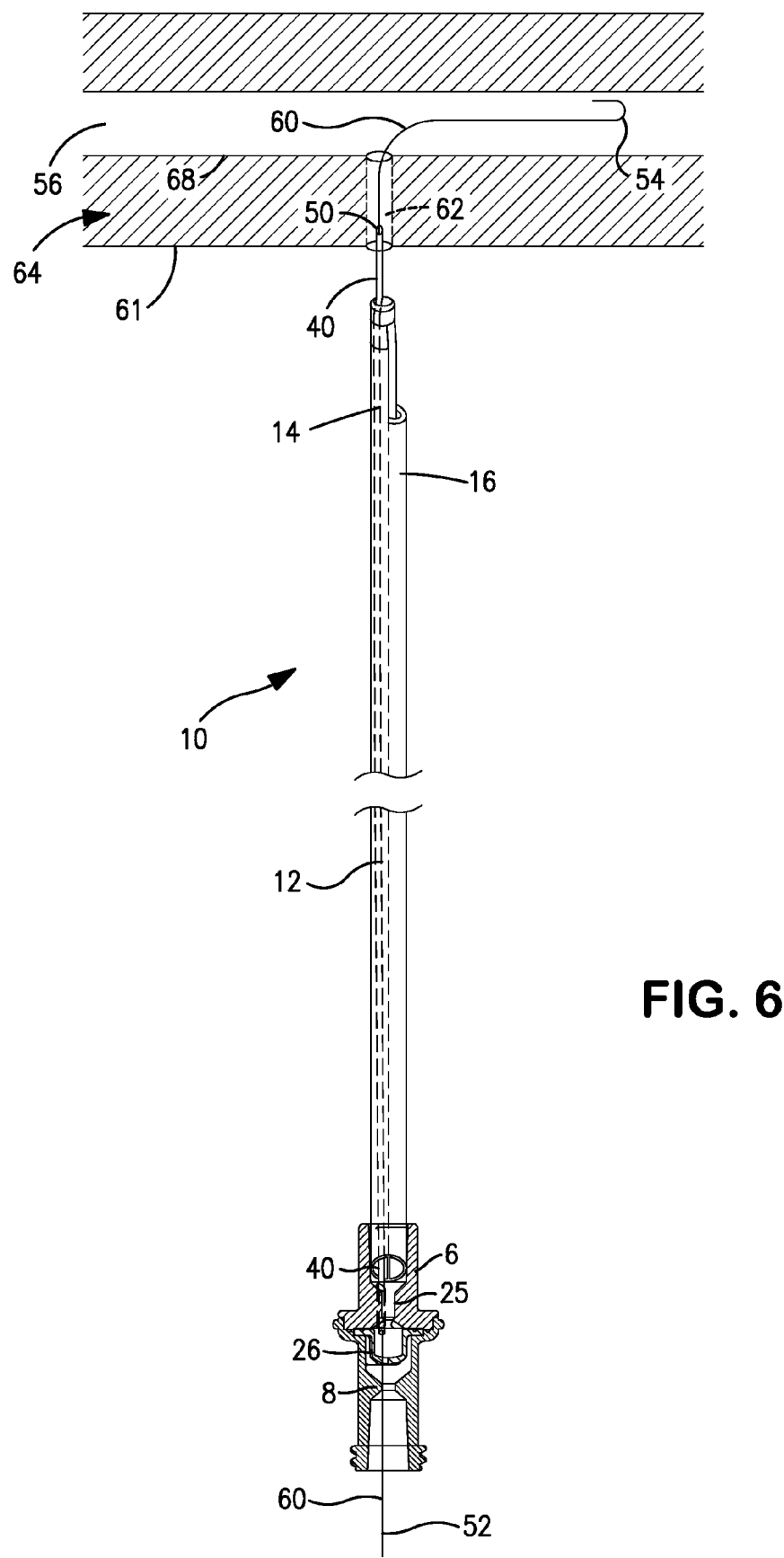
FIG. 6 is a perspective view of the insertion assembly in use.

Once the distal tip 54 of guidewire 60 is properly placed, the proximal end 52 of guidewire 60 is directed into the distal tip 50 of stiffener lumen 42. The insertion assembly 10 may then be advanced over the guidewire 60 to the point in the vasculature 56 of the patient where it is desired to place the distal tip of catheter 12. FIG. 6 shows the insertion assembly 10 with the guidewire 60 extending completely therethrough.

Placement of the stiffener 40 within catheter 12 causes the catheter 12 to be guided by guidewire 60 through the skin 61, subcutaneous tissue 64 and vessel wall 68 of the patient and into the vasculature 66. The stiffness of the stiffener 40 allows the soft, flexible catheter 12 to pass through the subcutaneous tissue 64 without the need for a catheter introducer.

In its closed position, valve 26 in valve hub portion 8 typically occludes substantially all liquid and gas, i.e. fluid, communication between the valve hub portion 8 and the remainder of the insertion assembly 10. Thus, valve 26 will substantially prevent a path from the atmosphere to the catheter 12, and thus to the vasculature of the patient, from being created. The duckbill arrangement will cause a net positive pressure differential on the valve hub portion 8 side of the valve 26 to force the duckbill together. Although some leakage through slit 28 may occur, especially if a guidewire is passed therethrough, such leakage will not pass a significant volume of gas. As such, even when guidewire 60 is disposed through valve slit 28, the valve 26 will still effectively occlude the catheter 12 and stiffener lumen 42.

At any point after the catheter 12 is inserted through lumen 62, stiffener 40 may be withdrawn and discarded by disengaging hub 7 from the proximal end 4 of catheter 12 and pulling stiffener 40 out of lumen 14. Proximal end 4 of catheter 12 may also be cut away from the remainder of the catheter 12 and removed along with the hubs 6 and 8 and the stiffener 40. Either action is accomplished while leaving the catheter 12 in place. Catheter 12 should be occluded by standard means prior to removal of valve 26. Guidewire 60 can be removed simultaneously with stiffener 40.

At a time after placement of the catheter fluid may be caused to enter insertion assembly 10 via distal tip 50 of stiffener 40. That is, once catheter 12 is inserted, blood may be aspirated from the patient's vasculature 56 into every space of the insertion assembly 10. This aspiration is typically achieved by attaching a syringe to connection threads 20 and causing a negative pressure in valve hub portion 8 that overcomes the threshold pressure of valve 26, passing the negative pressure into the catheter and stiffener lumens.

Figure 9:
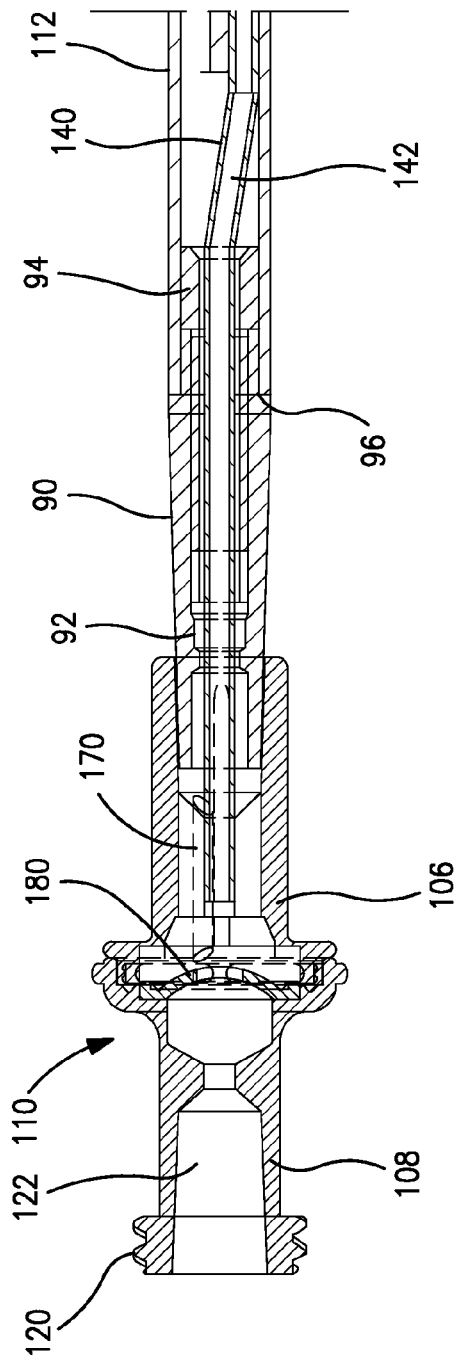
FIG. 9 is a cross-sectional detail view of an alternative embodiment of the insertion assembly showing some hidden-line detail.

FIG. 9 discloses an alternative embodiment of a catheter insertion assembly 110 in accordance with the present invention. Catheter insertion assembly 110 shown in FIG. 9 is similar to that shown in FIG. 8 except that a tunneling adapter 90 is used to secure the proximal end 104 of catheter 112 to the hub 107. Specifically, adapter 90 has a catheter attachment portion 94 which is inserted into the central bore of catheter 112 and secured to catheter 112 frictionally or by more secure means, e.g. adhesive or welding. At its opposite end, tunneling adapter 90 has an external diameter sized to be frictionally received in the distal portion of the central lumen 124 of stiffener hub 106. Tunneling adapter 90 may be disconnected from hub 106, resulting in catheter insertion assembly 110 being disconnected from the tunneling adapter 90 and catheter 112. This disconnection is required at a certain point during the catheter insertion procedure described above.

Figure 10:
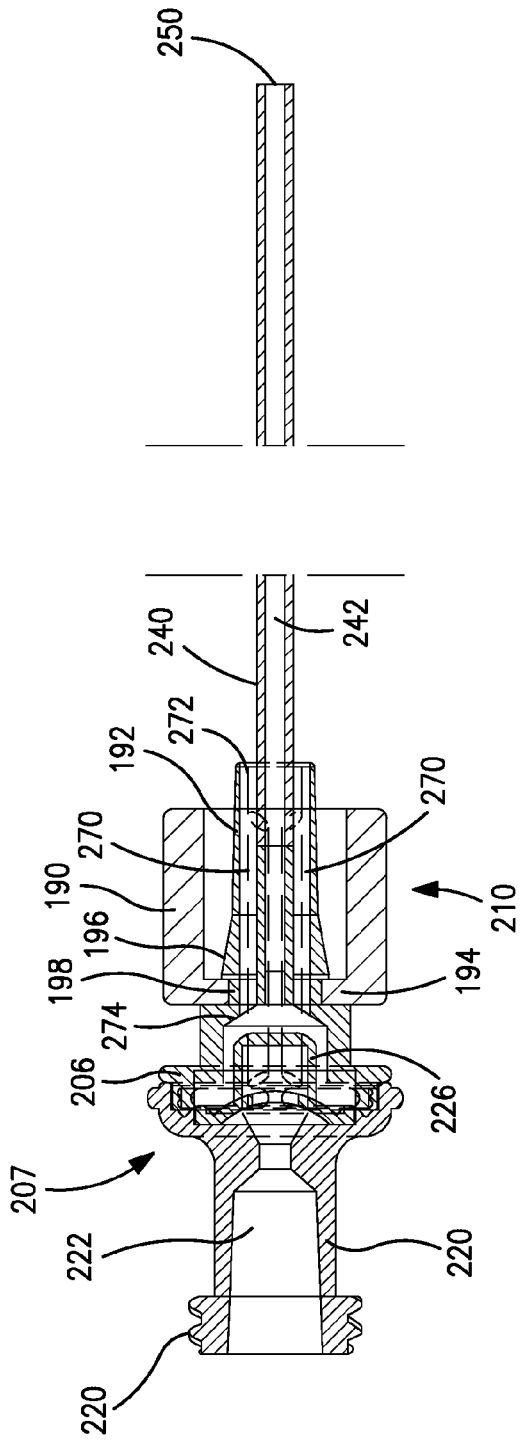
FIG. 10 is a cross-sectional view of an alternative embodiment of the insertion assembly hub and stiffener showing some hidden-line detail.
Figure 11:
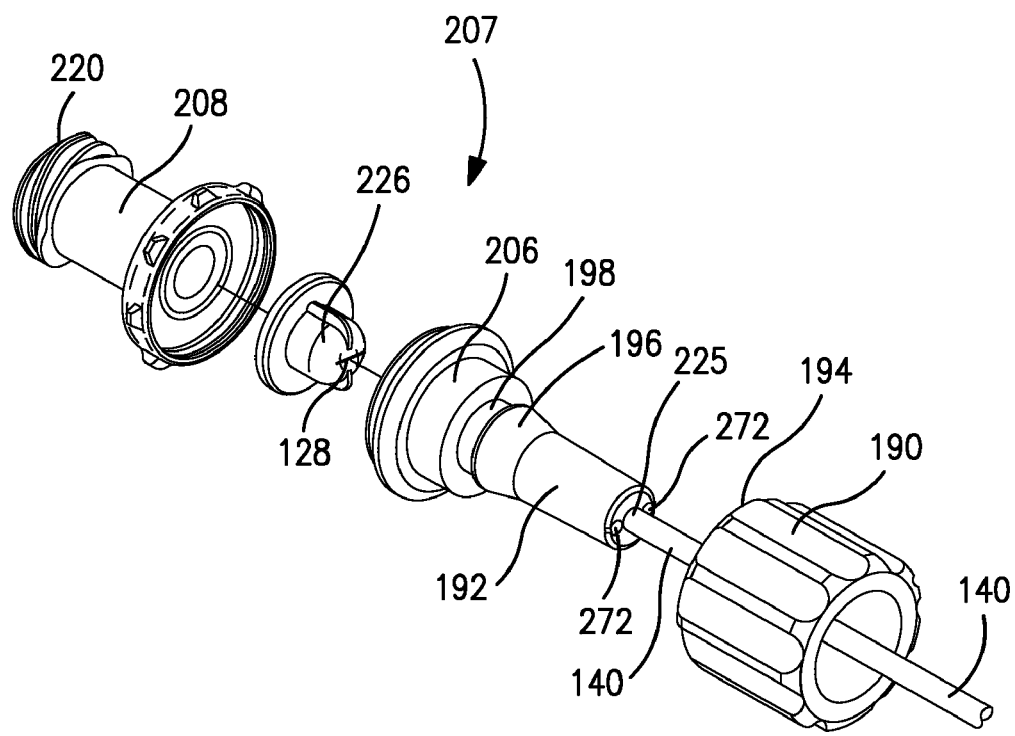
FIG. 11 is an exploded perspective view of the insertion hub shown in FIG. 10.

The structure and function of tunneling adapter 90 is described in U.S. Pat. No. 6,921,396 which is hereby incorporated by reference in its entirety. Specifically, once catheter insertion assembly 110 has served its function, as described above, tunneling adapter 90 and catheter 112 are disconnected from the assembly 110, which assembly 110 is then discarded. Tunneling adapter 90 may then be attached to a tunneling trocar (as shown in FIGS. 4 and 5 of U.S. Pat. No. 6,921,396) by means of a coupling portion 92. As shown at FIGS. 9-11 of U.S. Pat. No. 6,921,396, the tunneling trocar is used both to excavate a subcutaneous tunnel and dispose a portion of catheter 112 in the subcutaneous tunnel.

Figure 12:
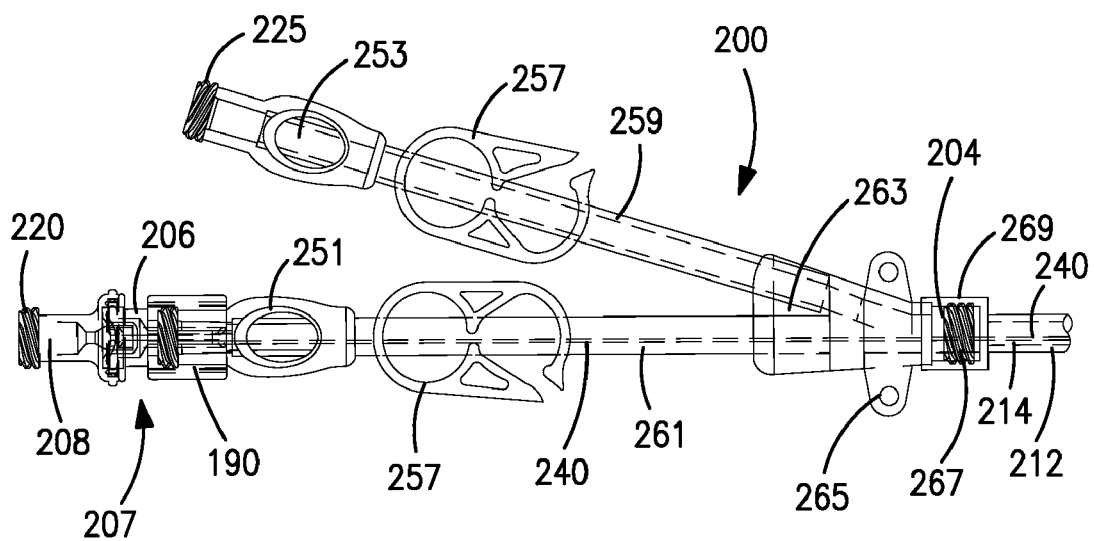
FIG. 12 is a side detail view of the insertion assembly hub shown in FIGS. 10 and 11 in use with a selectively attachable catheter hub and catheter.

FIGS. 10-11 show an embodiment of the present invention that is useful, for example, with the catheter apparatus shown in U.S. Pat. No. 6,638,242, previously incorporated herein by reference. U.S. Pat. No. 6,638,242 shows a two piece catheter assembly in FIG. 1, including a multilumen catheter 12 and selectively attachable hub assembly 20. The selectively attachable hub assembly of U.S. Pat. No. 6,638,242 is reproduced in FIG. 12 of the present application together with the alternative embodiment of the catheter insertion assembly 210 of FIGS. 10 and 11. The selectively attachable hub assembly 200 of FIG. 12 of the present application includes hub 263 and extension arms 259, 261.

Turning to the alternative embodiment of insertion assembly 210 shown in FIGS. 10 and 11, the insertion assembly 210 includes valve hub portion 208 and stiffener hub portion 206. Valve hub portion 208 contains valve 226, which may have the structure of valve 26 or valve 80 or any other suitable valve, and is not significantly changed from the previously described embodiments. Stiffener hub portion 206 has several changes and additional structures to permit attachment of the hub 207 to extension arm 261 of selectively attachable hub assembly 200. Specifically, stiffener hub portion 206 is further provided with a connection collar 190 disposed about extension cylinder 192. Extension cylinder 192 contains stiffener connection portion 225, irrigation tunnels 270 and irrigation tunnel distal holes 272. Connection collar 190 may be rotatably retained by stiffener hub portion 206 and is provided with any standard connection means, e.g. internal threads or luer lock, for connection to mating structures on connector 251 on extension arm 261 of selectively attachable hub assembly 200.

The rotatable connection between connection collar 190 and stiffener hub 206 is achieved through interaction between annular groove 198, wedge 196 on the external surface of stiffener hub extension cylinder 192 and annular detent 194 of connection collar 190. Annular detent 194 is sized to be rotatably received by annular groove 198 and retained on stiffener hub extension cylinder 192 by wedge 196. Stiffener 240 is attached to stiffener connection portion 225 of stiffener hub extension cylinder 192.

Returning to FIG. 12, the alternative embodiment of catheter insertion assembly 210 shown in FIGS. 10 and 11 is connected to the selectively attachable hub assembly 200. Specifically, connection collar 190 attaches insertion assembly 210 to connector 251 of extension arm 261. Stiffener 240 extends through connector 251, through the central lumen of extension arm 261, through hub 263 and through one lumen, e.g. lumen 214, of catheter 212. In use, stiffener 240 is utilized in the same manner as previously described. Once the distal portion of catheter 212 is properly placed in the patient, connection collar 190 may be disengaged from connector 251 and insertion assembly 210 may be detached and removed in its entirety from catheter 212 and catheter hub assembly 200. Insertion assembly 210 may then be discarded.

After insertion assembly 210 is removed from catheter hub assembly 200, the catheter 212 may be used. Alternatively, as disclosed in U.S. Pat. No. 6,638,242, catheter hub assembly 200 may also be detached from catheter 212 by disengaging catheter retention connector 269 from hub connection portion 267. Once disengaged from catheter hub assembly 200, the proximal end 204 of catheter 212 (referred to as the "distal end" in U.S. Pat. No. 6,638,242), may be subcutaneously tunneled or otherwise altered, e.g. cut to size or repaired. Catheter hub assembly 200 may then be easily reattached to catheter 212 in accordance with the disclosure of U.S. Pat. No. 6,638,242.

Now that the present invention has been described in detail, various modifications and improvements thereon will become readily apparent to those skilled in the art. Accordingly, the spirit and scope of the present invention is to be construed broadly and limited only by the appended claims, and not by the foregoing specification.

We claim:

1. A catheter insertion assembly comprising:
   a. a hub having a proximal end, a distal end and a lumen through the hub connecting the proximal and distal ends;
   b. a valve disposed in the lumen of the hub, said valve preventing substantially all fluid flow through the lumen in at least one direction below a pressure threshold;
   c. a stiffener comprising a proximal end, a distal end and a lumen, the proximal end of the stiffener is attached to the hub and the stiffener extends distally of the distal end of the hub, and the stiffener lumen is in fluid communication with the hub lumen;
   d. a narrowed portion of the hub lumen having approximately the same inside diameter as the outside diameter of the proximal end of the stiffener, wherein the proximal end of the stiffener is attached to the hub at the narrowed portion of the hub lumen; and
   e. one or more irrigation tunnels, wherein the hub lumen is divided by the narrowed portion into a distal hub portion and a proximal hub portion, the irrigation tunnels extend through the narrowed portion and form fluid communication between the distal hub portion and proximal hub portion.

2. The catheter insertion assembly of claim 1 further comprising a hole in the stiffener adjacent the proximal end of the stiffener, the hole providing fluid communication between the stiffener lumen and an area external to the stiffener wall.

3. The catheter insertion assembly of claim 1 which further includes a catheter disposed over the stiffener.

4. The catheter insertion assembly of claim 3 wherein the catheter is connected to the hub.

5. The catheter insertion assembly of claim 3 wherein the catheter is a multi-lumen catheter.

6. The catheter insertion assembly of claim 1 further comprising a catheter disposed over the stiffener and a tunneling adapter attached to the proximal end of the catheter, the tunneling adapter is removably attached to the hub.

7. An assembly for inserting a catheter comprising a catheter tube having one or more lumens extending from a proximal end of the catheter tube to adjacent a distal end of the catheter tube and an insertion device comprising:
   a. a stiffener disposed inside substantially the entire length of one of the catheter lumens of the catheter tube, the stiffener having a distal end and a proximal end;
   b. a hub having a distal end, a proximal end and a hub lumen extending from the distal to the proximal end, the hub further comprising:
      i. a stiffener connection point, the proximal end of the stiffener attached to the stiffener connection point;
      ii. a catheter connection point adjacent the distal end of the hub, the catheter detachably connected to the catheter connection portion adjacent of the hub; and
      iii. a valve bisecting the central lumen of the hub, the valve preventing substantially all fluid flow in at least one direction at a pressure below a threshold pressure; and
   c. one or more irrigation tunnels, wherein the stiffener connection point divides the hub lumen into a proximal hub portion and a distal hub portion, and further wherein the irrigation tunnels provide fluid communication between the distal hub portion and the proximal hub portion.

8. The assembly of claim 7 wherein at least one of the stiffener and the catheter is capable of receiving a guidewire and both the hub and the valve are capable of receiving the guidewire.

9. The assembly of claim 7 wherein the stiffener further comprising a stiffener lumen extending from the distal end to the proximal end of the stiffener.

10. The assembly of claim 9 further comprising a hole extending from the stiffener lumen to an external surface of the stiffener, the hole located adjacent the proximal end of the stiffener, the hole providing fluid communication between a portion of the connection hub lumen and the external surface of the stiffener through the stiffener lumen.

11. The assembly of claim 7 wherein the stiffness of the stiffener is sufficiently greater than the stiffness of the catheter to render a distal portion of the catheter insertable into the vasculature of a human patient.

12. The assembly of claim 7 further comprising fluid source retention threads adjacent the proximal end of the hub.

13. An insertion assembly for inserting a catheter comprising:
   a. a hub having:
      i. a proximal end;
      ii. a distal end; and
      iii. a lumen through the hub connecting the proximal and distal ends, the hub lumen comprising a valve seating portion and a stiffener connection portion;
   b. a valve disposed in the valve seating portion, said valve preventing substantially all fluid flow through the hub lumen in at least one direction when a pressure differential across the valve is below a threshold value;
   c. a stiffener attached to the stiffener connection portion, the stiffener comprising a wall encompassing a stiffener lumen, both the stiffener wall and the stiffener lumen extending the entire length of the stiffener; wherein the stiffener is disposed in a lumen of the catheter and a proximal end of the catheter is connected to the hub adjacent the distal end of the hub; and
   d. at least one irrigation tunnel, wherein the hub lumen is divided into a hub lumen distal portion and a hub lumen proximal portion connected by the irrigation tunnel for liquid exchange between the distal and proximal lumen portions.

14. The insertion assembly of claim 13 wherein the stiffener lumen is in fluid communication with at least a proximal portion of the hub lumen.

15. The insertion assembly of claim 13 further comprising a hole in the stiffener wall adjacent the proximal end of the stiffener, the hole providing fluid communication between the connection hub lumen and an area external to the stiffener wall.

16. An insertion assembly for inserting a catheter comprising:
   a. a hub having:
      i. a proximal end;
      ii. a distal end; and iii. a lumen through the hub connecting the proximal and distal ends, the hub lumen comprising a valve seating portion and a stiffener connection portion;

b. a valve disposed in the valve seating portion, said valve preventing substantially all fluid flow through the hub lumen in at least one direction when a pressure differential across the valve is below a threshold value;

c. a stiffener attached to the stiffener connection portion, the stiffener comprising a wall encompassing a stiffener lumen, both the stiffener wall and the stiffener lumen extending the entire length of the stiffener; wherein the stiffener is disposed in a lumen of the catheter and a proximal end of the catheter is connected to the hub adjacent the distal end of the hub;

d. a hole in the stiffener wall adjacent the proximal end of the stiffener, the hole providing fluid communication between the connection hub lumen and an area external to the stiffener wall; and e. the catheter is a multi-lumen catheter and the hole in the stiffener wall providing fluid communication between the connection hub lumen and an area external to the stiffener wall, including fluid communication with each lumen of the multi-lumen catheter.

* * * * *